United States Patent
Kobayashi et al.

(10) Patent No.: US 7,438,688 B2
(45) Date of Patent: Oct. 21, 2008

(54) APPARATUS AND METHOD FOR MEASURING PULSE RATE

(75) Inventors: Naoki Kobayashi, Tokyo (JP); Kenji Miyata, Tokyo (JP); Kazumasa Ito, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 255 days.

(21) Appl. No.: 11/510,616

(22) Filed: Aug. 28, 2006

(65) Prior Publication Data

US 2007/0060827 A1 Mar. 15, 2007

(30) Foreign Application Priority Data

Aug. 26, 2005 (JP) ............................ P2005-245501

(51) Int. Cl.
*A61B 5/02* (2006.01)
(52) U.S. Cl. ..................... 600/500; 600/481; 600/502
(58) Field of Classification Search .......... 600/485–528
See application file for complete search history.

(56) References Cited

U.S. PATENT DOCUMENTS

| | | | | |
|---|---|---|---|---|
| 3,934,577 A | * | 1/1976 | Romani | 600/453 |
| 4,086,917 A | * | 5/1978 | Burks et al. | 600/453 |
| 4,731,849 A | * | 3/1988 | Bloomfield, III | 381/67 |
| 4,955,379 A | * | 9/1990 | Hall | 600/336 |
| 5,170,791 A | * | 12/1992 | Boos et al. | 600/453 |
| 5,423,325 A | * | 6/1995 | Burton | 600/515 |
| 6,002,952 A | | 12/1999 | Diab et al. | |
| 6,022,321 A | | 2/2000 | Amano et al. | |
| 6,506,153 B1 | * | 1/2003 | Littek et al. | 600/301 |
| 6,542,764 B1 | | 4/2003 | Al-Ali et al. | |
| 6,699,194 B1 | | 3/2004 | Diab et al. | |
| 2003/0163054 A1 | | 8/2003 | Dekker | |
| 2004/0260186 A1 | * | 12/2004 | Dekker | 600/483 |
| 2006/0142667 A1 | * | 6/2006 | Munk | 600/528 |
| 2006/0155199 A1 | * | 7/2006 | Logier et al. | 600/509 |
| 2007/0004977 A1 | * | 1/2007 | Norris | 600/336 |

FOREIGN PATENT DOCUMENTS

| | | |
|---|---|---|
| JP | 1-153139 A | 6/1989 |
| JP | 10-507118 A | 7/1998 |
| WO | WO 96/12435 A2 | 5/1996 |
| WO | WO 02-43583 A2 | 6/2002 |
| WO | WO 03-063687 A2 | 8/2003 |

\* cited by examiner

*Primary Examiner*—Robert L. Nasser, Jr.
*Assistant Examiner*—Karen E Toth
(74) *Attorney, Agent, or Firm*—Sughrue Mion, PLLC

(57) ABSTRACT

In an apparatus adapted to measure a pulse rate of a subject, a plurality of band pass filters, each of which has a center frequency that is different from the others are provided. The band pass filters are connected in parallel to one another so as to be adapted to receive a first signal corresponding to a pulse wave of the subject and be operable to output a plurality of second signals each of which is obtained by filtering the first signal with each center frequency. A first processor is operable to obtain a fundamental frequency of the first signal. A selector is operable to select one of the second signals which is output from one of the band pass filters having such a center frequency that is closest to the fundamental frequency. A second processor is operable to calculate the pulse rate from the selected one of the second signals.

14 Claims, 5 Drawing Sheets

APPARATUS AND METHOD FOR MEASURING PULSE RATE

BACKGROUND OF THE INVENTION

The present invention relates to an improvement in signal processing in a pulse meter and a pulse photometer used for evaluation of functions of a respiratory system and a circulatory system.

In medical fields, an apparatus called a photoplethysmograph for measuring a pulse rate on the basis of a waveform of a pulse wave is used. An apparatus for measuring an oxygen saturation ($SpO_2$), an apparatus for measuring the concentration of dyshemoglobin such as carboxyhemoglobin and methemoglobin, and an apparatus for measuring dye concentration injected in the blood, and the like are known as pulse photometers for providing information on a pulse rate and a blood substance concentration. An apparatus adapted to measure an oxygen saturation $SpO_2$ is called a pulse oximeter and is used extensively in medical fields and sport fields.

The principle of the pulse photometer is to determine the concentration of an object material from a pulse wave data signal obtained by causing a living tissue to transmit or reflect light beams, which have a plurality of wavelengths respectively correspond to different absorbances of the object material, and by continuously measuring an intensity of transmitted or reflected light. In a case where noises are mixed in pulse wave data, calculation of a correct concentration or pulse rate cannot be achieved. Consequently, there is an anxious that an erroneous treatment may be performed.

Japanese Patent Publication No. 1-153139A discloses a pulse oximeter having a band pass filter to reduce such noises. Japanese Patent Publication No. 10-507118T discloses a method of correlating two signals for the same purpose.

However, these techniques utilize adaptive filters, the characteristics of each of which are changed according to the fundamental frequency of a pulse wave. Thus, a closed loop configuration may cause unstable oscillation. Also, these techniques have problems that oscillations due to a transient response of the filter occur, and that a response time of the filter becomes long. Thus, it is difficult to generate synchronous sounds by stably measuring a pulse rate in a real time manner.

SUMMARY OF THE INVENTION

It is therefore an object of the invention to provide an apparatus and a method for measuring a pulse rate, which are enabled to measure, even in a case where noises are mixed into pulse waves, a pulse rate with high accuracy thereby to generate sounds in synchronization with pulse waves in a real time manner.

In order to achieve the above object, according to the invention, there is provided an apparatus, adapted to measure a pulse rate of a subject, comprising:

a plurality of band pass filters, each of which has a center frequency that is different from the others, the band pass filters being connected in parallel to one another so as to be adapted to receive a first signal corresponding to a pulse wave of the subject and be operable to output a plurality of second signals each of which is obtained by filtering the first signal with each center frequency;

a first processor, operable to obtain a fundamental frequency of the first signal;

a selector, operable to select one of the second signals which is output from one of the band pass filters having such a center frequency that is closest to the fundamental frequency; and a second processor, operable to calculate the pulse rate from the selected one of the second signals.

With this configuration, noises, whose frequencies are outside the band of the band pass filter outputting the selected one of the second signal, can be removed. Consequently, a false detection of the pulse rate due to the noise can be prevented.

In addition, output waveforms of each of the filters can always be used without unstable operations, such as a step response and an impulse response.

The first processor may be operable to perform a fast Fourier transform processing to obtain the fundamental frequency.

The first processor may be operable to determine a frequency having a maximum amplitude as the fundamental frequency.

The second processor may be operable to calculate the pulse rate on the basis of an interval between time points at which a voltage of the selected one of the second signals either decreases to zero or increases to zero.

The apparatus may further comprise a sound generator, operable to generate a sound at every one of the time points.

In this case, the pulse rate can aurally be recognized in a real time manner.

The apparatus may further comprise a noise separator, operable to separate noise superimposed on the first signal.

In this case, even when a noise is mixed into the first signal, the fundamental frequency of the first signal can accurately be detected, hence the pulse rate can be calculated.

The first signal may be at least one of a red light signal and an infrared light signal supplied from a pulse photometer.

According to the invention, there is also provided a method for measuring a pulse rate of a subject, comprising:

providing a plurality of band pass filters, each of which has a center frequency that is different from the others, the band pass filters being connected in parallel to one another so as to be adapted to receive a first signal corresponding to a pulse wave of the subject and be operable to output a plurality of second signals each of which is obtained by filtering the first signal with each center frequency;

obtaining a fundamental frequency of the first signal;

selecting one of the second signals which is output from one of the band pass filters having such a center frequency that is closest to the fundamental frequency; and calculating the pulse rate from the selected one of the second signals.

A fast Fourier transform processing may be performed to obtain the fundamental frequency.

A frequency having a maximum amplitude which is obtained by the fast Fourier transform processing may be determined as the fundamental frequency.

The pulse rate may be calculated on the basis of an interval between time points at which a voltage of the selected one of the second signals either decreases zero or increases to zero.

The method may further comprise generating a sound at every one of the time points.

The method may further comprise separating noise superimposed on the first signal.

The first signal may be at least one of a red light signal and an infrared light signal supplied from a pulse photometer.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE EMBODIMENTS

Embodiments of the invention will be described below in detail with reference to the accompanying drawings.

Figure 1:
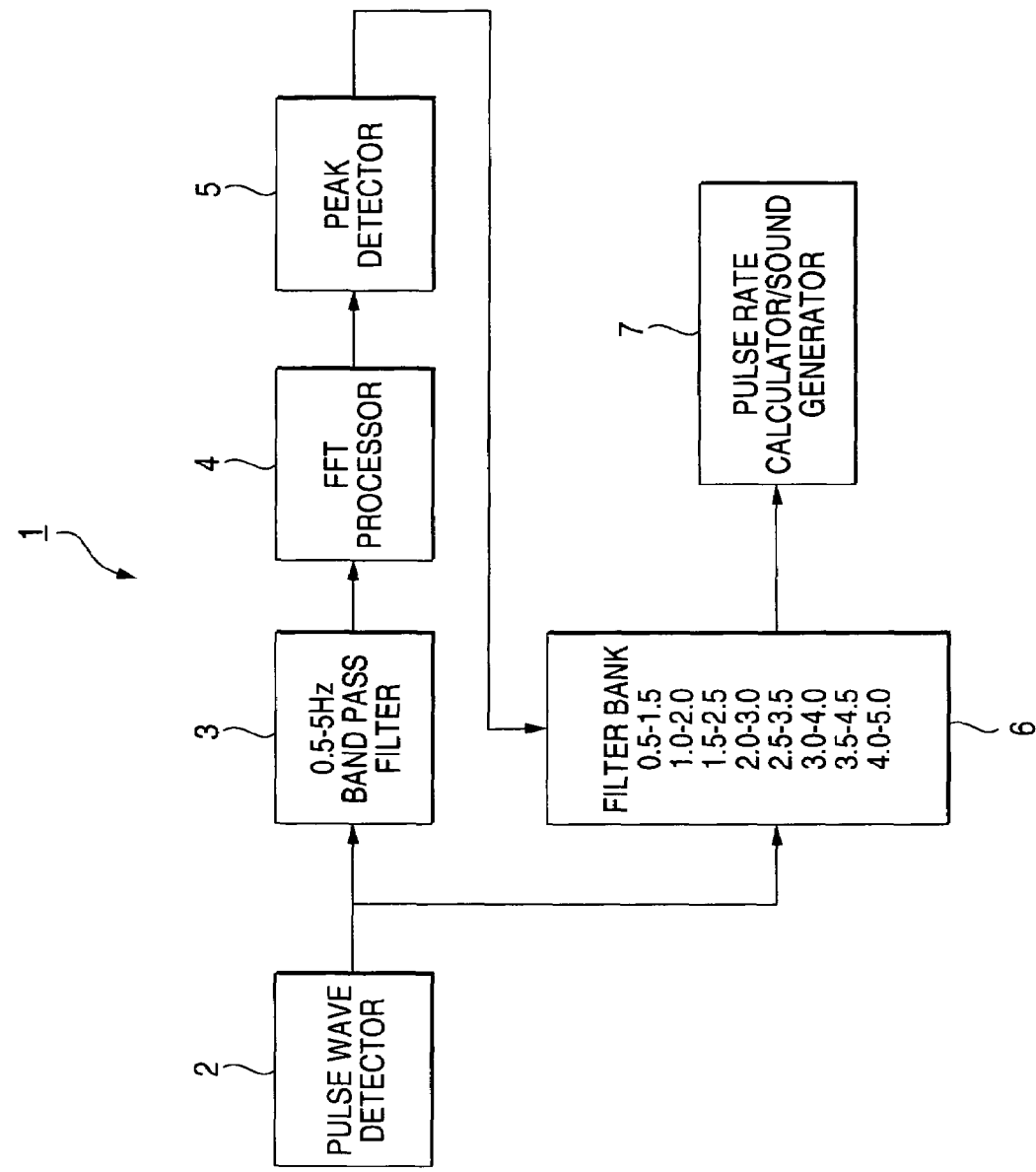
FIG. 1 is a block diagram showing a main part of a pulse rate measuring apparatus according to a first embodiment of the invention.

As shown in FIG. 1, in a pulse rate measuring apparatus 1 according to a first embodiment of the invention, an FFT processor 4 performs FFT processing on output signals of a band pass filter 3 according to programs stored in a ROM (not shown) and converts an output signal on a time-axis basis into an output signal on a frequency-axis basis. Incidentally, a signal to be measured can be decomposed into a plurality of frequency components by performing FFT processing. Thus, an amplitude spectrum can be obtained. A peak detector 5 obtains a frequency, at which the amplitude has a maximum value, from the amplitude spectrum obtained by the FFT processor 4.

A filter bank 6 has a configuration in which plural band pass filters are provided in parallel to one another. In this embodiment, the filter bank 6 includes 8 band pass filters, each of which has the lowest frequency at a corresponding one of frequencies obtained by dividing a frequency band of 0.5 Hz to 5 Hz including a pulse wave signal from a pulse wave detector 2 by 0.5 Hz and which also has a band width of 1 Hz. That is, the filter bank 6 includes 8 band pass filters respectively having frequency bands of 0.5 H to 1.5 Hz, 1.0 Hz to 2.0 Hz, 1.5 Hz to 2.5 Hz, 2.0 Hz to 3.0 Hz, 2.5 Hz to 3.5 Hz, 3.0 Hz to 4.0 Hz, 3.5 Hz to 4.5 Hz, and 4.0 Hz to 5.0 Hz. The pulse rate measuring apparatus 1 detects a frequency, at which the amplitude has a maximum value, from the amplitude spectrum obtained by the FFT processor 4 according to the programs stored in the ROM. Also, the pulse rate measuring apparatus 1 selects an output signal of the single band pass filter having a center frequency that is closest to the frequency, at which the amplitude has a maximum value.

A pulse rate calculator/sound generator 7 is adapted to calculate a pulse rate for a predetermined time period on the basis of an output signal of the selected single band pass filter according to an output of the peak detector 5. More specifically, the pulse rate calculator/sound generator 7 detects leading zero crossing points of output signals of the single band pass filter and calculates an interval $T_n$ between the zero crossing points. Further, the pulse rate calculator/sound generator 7 calculates an instantaneous pulse rate PR from $T_n$ and sets the average of the instantaneous pulse rate PR in a predetermined time to be an average pulse rate.

Next, a process of measuring a pulse rate performed by the pulse rate measuring apparatus will be described below.

Figure 2:
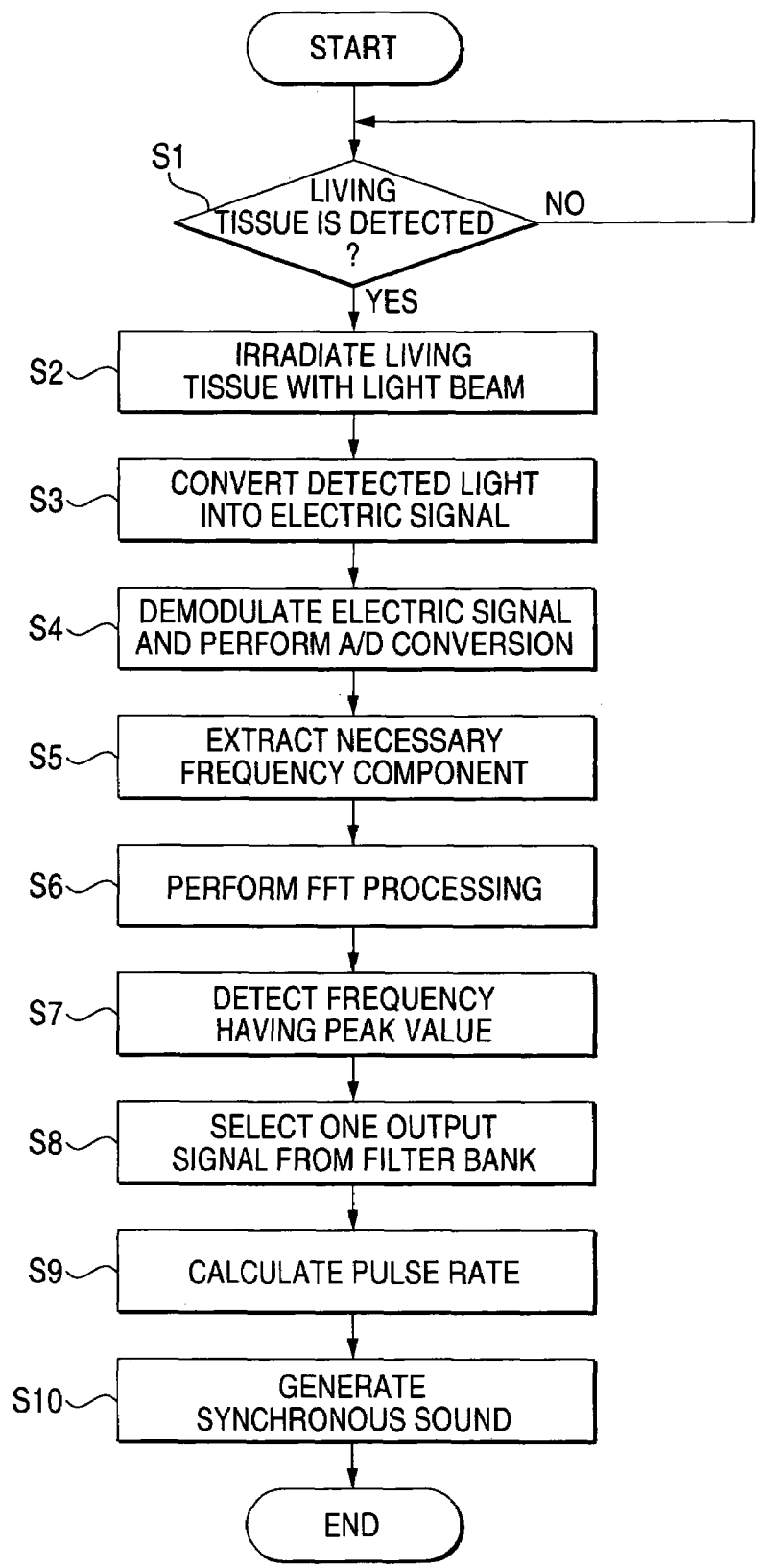
FIG. 2 is a flowchart showing processing for measuring a pulse rate and generating a synchronous sound.

As shown in FIG. 2, when the pulse rate measuring apparatus 1 is activated, a standby state is effected in step S1 until a living tissue is mounted in a probe (not shown) in the pulse rate measuring apparatus 1. When the pulse rate measuring apparatus 1 detects the living tissue, an LED is driven by an LED driver (not shown). That is, light having a predetermined wavelength is emitted with predetermined timing in step S2.

Subsequently, in step S3, a photodiode receives light transmitted by the living tissue, so that an optical signal is converted into an electrical signal. Then, the electrical signal is converted to a voltage by a current-voltage converter. Subsequently, the pulse wave signal corresponding to a waveform extracted with predetermined timing by a pulse wave demodulation circuit is converted into a digital value by an A/D converter in step S4. Then, the filtering of the pulse wave signal, whose signal level has been converted into a digital value, is performed by the band pass filter 3. That is, the band pass filter 3 extracts signal components in the frequency band of frequencies from 0.5 Hz to 5 Hz, which includes the pulse wave signal from the pulse wave detector 2, in step S5.

In step S6, the FFT processor 4 performs an operation utilizing FFT processing according to the programs relating to the FFT processing, which are stored in the ROM.

Subsequently, the peak detector 5 detects a frequency, at which the amplitude has a maximum value, from the frequency spectrum as the fundamental frequency of the pulse wave signal from the pulse wave detector 2 in step S7. In step S8, the peak detector 5 selects, from output signals of the eight band pass filters 6, an output signal of the single band pass filter whose center frequency is closest to the fundamental frequency of the pulse wave signal from the pulse wave detector 2 detected in step S7.

Incidentally, a method of calculating an average value of frequencies, at each of which the amplitude has a maximum value, over a predetermined past time period, or a method of determining a frequency, at which the amplitude has a maximum value with predetermined timing, is set as a method of detecting the fundamental frequency of the pulse wave signal from the pulse wave detector 2. Also, the method of detecting the fundamental frequency of the pulse wave signal from the pulse wave detector 2 is set so that even in a case where the fundamental frequency of the pulse wave signal from the pulse wave detector 2 belongs to a plurality of band pass filters among the 8 band pass filters, only one of the plurality of band pass filters is selected without exception.

Figure 3:
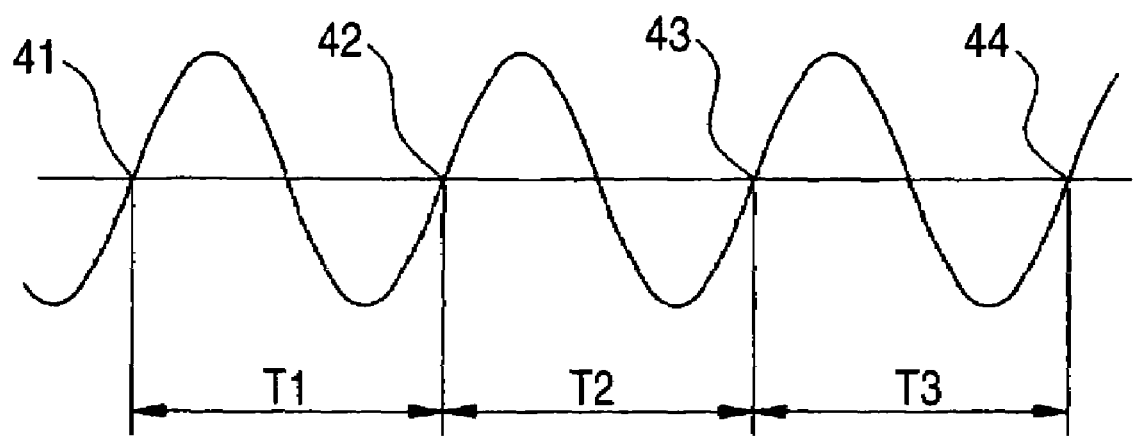
FIG. 3 is a waveform chart showing a waveform obtained by the processing of FIG. 2.

Subsequently, the pulse rate calculator/sound generator 7 detects zero crossing points 41, 42, 43, and 44 in a predetermined time period from the pulse wave signal passed through the selected one of the band pass filters, as shown in FIG. 3. The zero crossing point is defined as a time point at which the voltage of the pulse wave signal either decreases to zero or increases to zero. Then, the pulse rate calculator/sound generator 7 calculates the intervals T1, T2, and T3 between the zero crossing points 41, 42, and 43, and 44. Subsequently, the pulse rate calculator/sound generator 7 calculates the instantaneous pulse rates PR1=60/T1, PR2=60/T2, and PR3=60/T3. Then, the pulse rate calculator/sound generator 7 calculates an average pulse rate by averaging these instantaneous pulse rates in step S9. The calculated average pulse rate is indicated in a display. Also, each time when the zero crossing points are detected, the pulse rate calculator/sound generator 7 generates a synchronous sound in step S10.

Incidentally, analog filters may be used as the band pass filter 3 and the filter bank 6 in this embodiment. Further, the filter bank 6 can be constituted with multi-rate processing using Wavelet transformation.

In this embodiment, the pulse rate measuring apparatus 1 calculates a pulse rate only from a signal obtained by transmitting light having a single wavelength. However, in a case where the pulse rate measuring apparatus 1 is installed in a pulse oximeter, at least one of infrared light IR and red light R may be used. Incidentally, when the infrared light IR having a high amplitude value is employed, a peak value can easily been obtained.

Figure 4A:
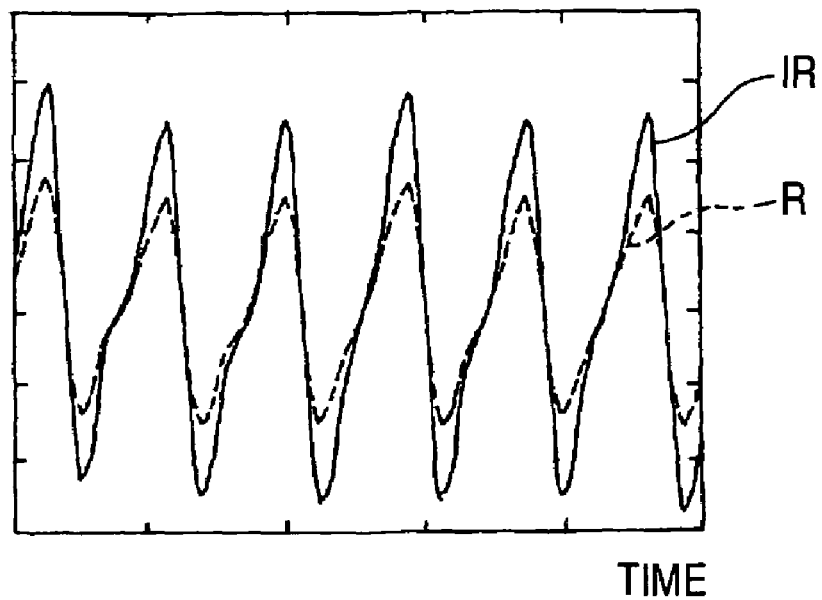
FIGS. 4A and 4B are waveform charts showing waveforms obtained by processing executed in a pulse rate measuring apparatus according to a modified example of the first embodiment.
Figure 4B:
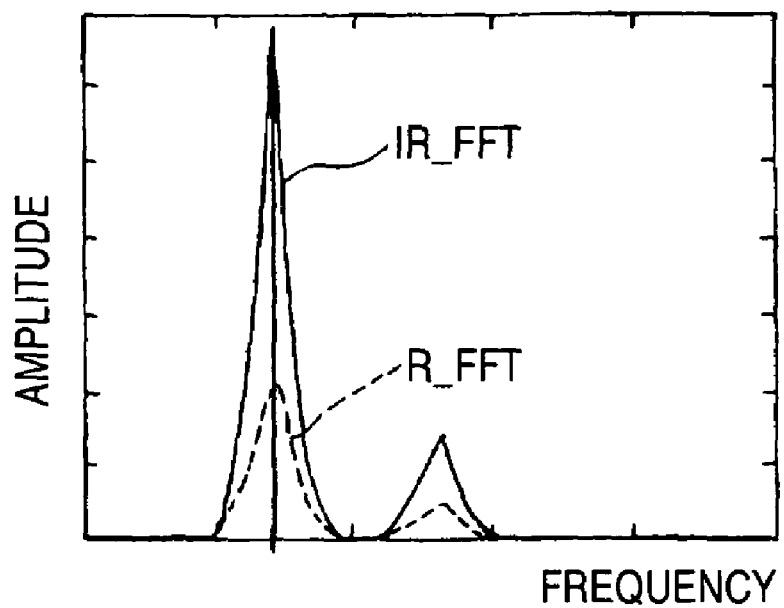

FIGS. 4A and 4B show waveforms of a pulse wave signal in a case where a method of alternately transmitting two kinds of light beams (red light R and infrared light IR) is employed. FIG. 4A shows a condition after the filtering of the pulse wave signal is performed, in a case where almost no noise due to a body motion is mixed into the pulse wave. FIG. 4B shows an amplitude spectrum (R_FET and IR_FET) obtained by applying FFT processing to the signals R and IR shown in FIG. 4A. In the case where almost no noise due to a body motion is mixed into the pulse wave, the magnitude spectrum shows a maximum value of the amplitude at the frequency of the pulse wave signal. A pulse wave having a waveform shown in FIG. 3 can be obtained by extracting a signal of this frequency from the filter bank.

A state, in which almost no noise due to the body motion is mixed into the pulse wave signal from the pulse wave detector 2, has been described in the foregoing description of this embodiment. However, even in a case where noise due to a body motion is mixed into the pulse wave signal from the pulse wave detector 2, the fundamental frequency of the pulse wave signal can be detected by separating the pulse wave signal and the noise due to the body motion from each other through the use of a well-known signal separation method.

Figure 5:
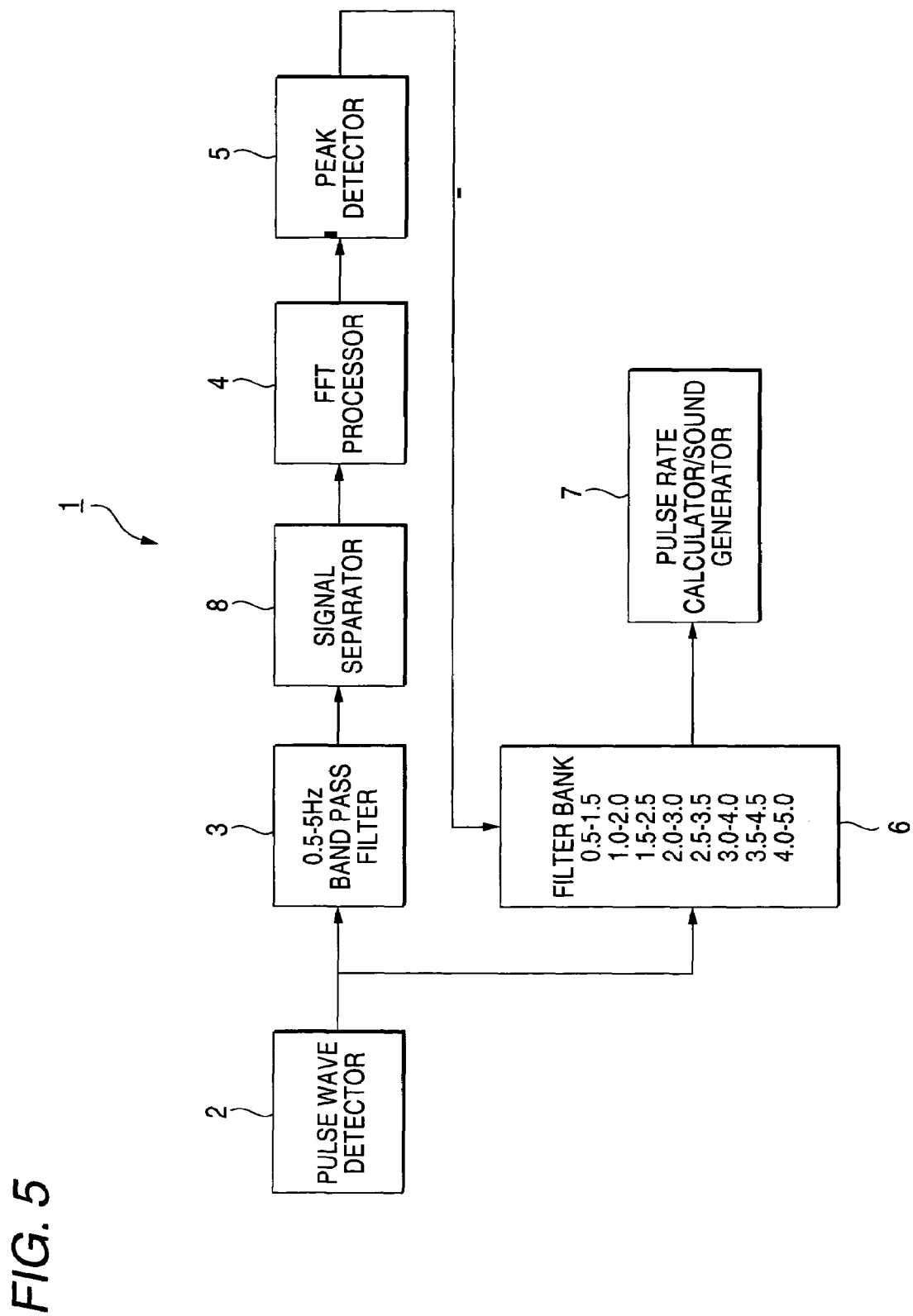
FIG. 5 is a block diagram showing a main part of a pulse rate measuring apparatus according to a second embodiment of the invention.

Such a configuration will be described as a second embodiment of the invention with reference to FIG. 5. Components similar to those in the first embodiment will be designated by the same reference numerals and repetitive explanations for those will be omitted.

A signal separator 8 is operative to separate the pulse wave signal from the pulse wave detector 2 into a pulse wave signal, which includes no noises, and noises due to a body motion. A signal separation method disclosed in the Japanese Patent Publication No. 2005-95581A or another well-known method may be employed as a signal separation processing.

Therefore, even when a noise is mixed into the pulse wave signal from the pulse wave detector 2, the frequency of the pulse wave signal can accurately be detected by using both of the FFT processing and the signal separation processing.

As described above, according to the invention, since a plurality of band pass filters differing in center frequency from one another, into which pulse wave signals detected from a living tissue are inputted, are provided, a pulse rate is measured by using a signal having passed through the band pass filter, which has a frequency close to the fundamental frequency of the pulse wave signal as a center frequency. Therefore, noises, whose frequencies are outside the band of the band pass filter, can be eliminated. Consequently, an occurrence of false detection of the pulse rate due to the noise can be prevented.

Further, since the pulse wave signal from the pulse wave detector 2 is subjected to the FFT processing and a frequency which is close to the fundamental frequency of the pulse wave signal is detected upon selection of a suitable band pass filter, a specific (fundamental) frequency component can easily be detected from the plurality of frequency components included in the pulse wave signal from the pulse wave detector 2. Also, since the pulse wave signal is respectively inputted to the plurality of band pass filters connected in parallel to one another, output waveforms of each of the filters can always be used without unstable operations, such as a step response and an impulse response.

Moreover, since the pulse rate calculator/sound generator 7 generates synchronous sounds every time when the signal level of the selected output signal crosses zero, the pulse wave signals can aurally be recognized in a real time manner.

Although the present invention has been shown and described with reference to specific preferred embodiments, various changes and modifications will be apparent to those skilled in the art from the teachings herein. Such changes and modifications as are obvious are deemed to come within the spirit, scope and contemplation of the invention as defined in the appended claims.

What is claimed is:

1. An apparatus, adapted to measure a pulse rate of a subject, comprising:
    a plurality of band pass filters, each of which has a center frequency that is different from the others, the band pass filters being connected in parallel to one another so as to be adapted to receive a first signal corresponding to a pulse wave of the subject and be operable to output a plurality of second signals each of which is obtained by filtering the first signal with each center frequency;
    a first processor, operable to obtain a fundamental frequency of the first signal;
    a selector, operable to select one of the second signals which is output from one of the band pass filters having such a center frequency that is closest to the fundamental frequency; and
    a second processor, operable to calculate the pulse rate from the selected one of the second signals.

2. The apparatus as set forth in claim 1, wherein:
    the first processor is operable to perform a fast Fourier transform processing to obtain the fundamental frequency.

3. The apparatus as set forth in claim 2, wherein:
    the first processor is operable to determine a frequency having a maximum amplitude as the fundamental frequency.

4. The apparatus as set forth in claim 1, wherein:
    the second processor is operable to calculate the pulse rate on the basis of an interval between time points at which a voltage of the selected one of the second signals either decreases to zero or increases to zero.

5. The apparatus as set forth in claim 4, further comprising:
    a sound generator, operable to generate a sound at every one of the time points.

6. The apparatus as set forth in claim 1, further comprising:
    a noise separator, operable to separate noise superimposed on the first signal.

7. The apparatus as set forth in claim 6, wherein:
    the first signal is at least one of a red light signal and an infrared light signal supplied from a pulse photometer.

8. A method for measuring a pulse rate of a subject, comprising:
    providing a plurality of band pass filters, each of which has a center frequency that is different from the others, the band pass filters being connected in parallel to one another so as to be adapted to receive a first signal corresponding to a pulse wave of the subject and be operable to output a plurality of second signals each of which is obtained by filtering the first signal with each center frequency;

obtaining a fundamental frequency of the first signal;
selecting one of the second signals which is output from one of the band pass filters having such a center frequency that is closest to the fundamental frequency; and
calculating the pulse rate from the selected one of the second signals.

9. The method as set forth in claim 8, wherein:
a fast Fourier transform processing is performed to obtain the fundamental frequency.

10. The method as set forth in claim 9, wherein:
a frequency having a maximum amplitude which is obtained by the fast Fourier transform processing is determined as the fundamental frequency.

11. The method as set forth in claim 8, wherein:
the pulse rate is calculated on the basis of an interval between time points at which a voltage of the selected one of the second signals either decreases to zero or increases to zero.

12. The method as set forth in claim 11, further comprising:
generating a sound at every one of the time points.

13. The method as set forth in claim 8, further comprising:
separating noise superimposed on the first signal.

14. The method as set forth in claim 13, wherein:
the first signal is at least one of a red light signal and an infrared light signal supplied from a pulse photometer.

* * * * *